United States Patent [19]

Sapre

[11] Patent Number: 4,590,320
[45] Date of Patent: May 20, 1986

[54] CONVERSION OF METHANOL TO OLEFINS IN A TUBULAR REACTOR WITH LIGHT OLEFIN CO-FEEDING

[75] Inventor: Ajit V. Sapre, West Deptford, N.J.

[73] Assignee: Mobil Oil Corporation, New York, N.Y.

[21] Appl. No.: 765,579

[22] Filed: Aug. 14, 1985

Related U.S. Application Data

[63] Continuation of Ser. No. 646,262, Aug. 31, 1984, abandoned.

[51] Int. Cl.$^4$ .............................................. C07C 1/20
[52] U.S. Cl. ..................... 585/324; 585/315; 585/327; 585/408; 585/469; 585/640; 585/733
[58] Field of Search ............... 585/315, 316, 324, 327, 585/408, 469, 640, 639, 733

[56] References Cited

U.S. PATENT DOCUMENTS

| | | | |
|---|---|---|---|
| 3,894,106 | 7/1975 | Chang et al. | 585/408 |
| 3,931,349 | 1/1976 | Kuo | 585/640 |
| 3,979,472 | 9/1976 | Butter | 585/408 |
| 4,025,571 | 5/1977 | Lago | 585/408 |
| 4,025,572 | 5/1977 | Lago | 585/408 |
| 4,025,575 | 5/1977 | Chang et al. | 585/640 |
| 4,035,430 | 7/1977 | Dwyer et al. | 585/322 |
| 4,052,479 | 10/1977 | Chang et al. | 585/640 |
| 4,058,576 | 11/1977 | Chang et al. | 585/640 |
| 4,060,568 | 11/1977 | Rodewald | 585/640 |
| 4,100,219 | 7/1978 | Rodewald | 585/640 |
| 4,148,835 | 4/1979 | Chen et al. | 585/640 |
| 4,232,179 | 11/1980 | Valladeres Barrocas | 585/640 |
| 4,238,631 | 12/1980 | Daviduk et al. | 585/469 |
| 4,247,731 | 1/1981 | Wunder et al. | 585/640 |

Primary Examiner—John Doll
Assistant Examiner—A. Pal
Attorney, Agent, or Firm—Alexander J. McKillop; Michael G. Gilman; Dennis P. Santini

[57] ABSTRACT

The operating performance of a tubular reactor system designed for the exothermic conversion of methanol to light olefins is improved by cofeeding small quantities of light olefins with the methanol feed, whereby a more controllable operation is achieved. Catalyst activity and cycle length also improves significantly. The light olefins can be produced in situ during conversion.

25 Claims, 4 Drawing Figures

KINETICS COMPARISON

CONVERSION OF METHANOL TO OLEFINS IN A TUBULAR REACTOR WITH LIGHT OLEFIN CO-FEEDING

This is a continuation of copending application Ser. No. 646,262, filed on Aug. 31, 1984, now abandoned.

BACKGROUND OF THE INVENTION

1. Field of the Invention

This invention relates to the production of olefins from a lower aliphatic alcohol, its corresponding ether or mixtures thereof. More particularly, it relates to the catalytic conversion of a methanol feed to an olefinic product. This invention especially relates to improvements in the conversion of a methanol feed to an olefinic product in a tubular reactor system.

2. Description of the Prior Art

The petrochemical industry has undergone tremendous growth in the past few decades. The production of synthetic fibers, plastics and petrochemicals by this and allied industries has steadily grown, at least in part, because of the availability of increasing supplies of inexpensive petrochemical raw materials, such as ethylene, propylene and other olefins. The principal source of ethylene at the present time is from steam cracked petroleum naphtha. The manufacture of polyethylene and styrene monomer utilizes a significant portion of this ethylene feed.

The ever-increasing demand for olefinic feedstocks has periodically caused a shortage of these basic raw materials, either because of a limitation in petroleum feedstocks of suitable quality or a limitation in naphtha cracking capacity. An alternate source of ethylene from non-petroleum sources is one obvious means of keeping pace with the demand for ethylene and other olefins.

In recent years, the patent art has disclosed that methanol and/or dimethyl ether, which may be obtained from coal, natural gas or biomass, can be converted to more complex hydrocarbons, such as olefins and aromatics, by utilizing a novel group of zeolites, exemplified by ZSM-5 zeolites. Ethylene is one of the olefinic hydrocarbons which may be obtained in this catalytic conversion. The reaction is highly exothermic and the olefins initially formed have a tendency to undergo further reaction to produce aromatic hydrocarbons useful in the production of motor gasoline. A large body of this patent art is concerned with various aspects of the conversion of methanol and/or dimethyl ether to light olefins, particularly ethylene.

The production of olefins from aliphatic ethers by catalytic conversion with a HZSM-5 zeolite catalyst is disclosed in U.S. Pat. No. 3,894,106 to Chang et al.

U.S. Pat. No. 3,979,472 to Butter discloses the conversion of lower alcohols and their ethers with a composite of antimony oxide and a ZSM-5 zeolite to produce a mixture of ethylene, propylene and mononuclear aromatics. U.S. Pat. No. 4,025,572 to Lago discloses that ethylene selectivity can be improved by diluting ZSM-5 with an inert diluent, while a similar result is achieved, according to U.S. Pat. No. 4,025,575 to Chang et al, through use of subatmospheric partial pressure of the feed. Selectivity of ethylene is also improved by employing ZSM-5 zeolite in large crystal form of at least 1 micron, either alone (U.S. Pat. No. 4,025,571 to Lago) or in combination, with added metals (U.S. Pat. No. 4,148,835 to Chen et al). Better selectivity is also obtained by interdispersing amorphous silica within the interior of the crystalline structure of the zeolite catalyst (U.S. Pat. Nos. 4,060,568 and 4,100,219 to Rodewald).

Although the above-described conversions perform exceptionally well and are unusually effective at converting lower aliphatic alcohols to olefinic hydrocarbons, it has been found that these conversions are exothermic to varying degrees, depending on the particular reactant. For example, the amount of heat generated in the conversion of the lower alcohols to hydrocarbon product may be estimated to be in the ranges shown.

| Alcohol Reactant | Heat Produced, BTU per lb of Hydrocarbon Product |
| --- | --- |
| Methanol | 1000–2000 |
| Ethanol | 200–620 |
| Propanol | 15–360 |

While it is desirable that a reaction be exothermic, since this obviates the need for an external source of heat to drive the reaction, large heat generation loads can require substantial investment in complex reactors with extensive internal cooling means. It can be seen from the above Table that the conversion of methanol, and to a lesser degree of ethanol, could be considered excessively exothermic in this regard. Furthermore, because of the inherent character and efficiency of the above-described crystalline aluminosilicate zeolite catalysts, the reaction of methanol, and to a lesser degree of ethanol, tend to be self-accelerating, thereby creating excessively hot local regions, where the reaction tends to go to completion, in the catalyst bed. These highly exothermic reactions can result in high catalyst aging rates, and possibly cause thermal damage to the catalyst. Furthermore, such high temperatures could cause an undesirable product distribution to be obtained. Therefore, it is critical in the conversion of methanol to useful products to provide sufficient heat dissipating facilities so that temperatures encountered in any portion of the catalyst sequence are restricted within predetermined limits.

Additionally, it is generally good engineering practice to conduct reactant conversions at elevated pressures to more effectively utilize the reactor volume and attendant equipment. With a methanol charge, however, elevated pressures tend to produce increased quantities of 1,2,4,5-tetramethylbenzene (durene), an undesirable by-product, while lower pressures, e.g., less than 50 psig, favor the production of light olefins.

Various techniques have been employed in controlling the exothermic heat released in the catalytic conversion of methanol: U.S. Pat. Nos. 3,931,349 to Kuo (use of light hydrocarbon diluents as heat sink for conversion of methanol-to-gasoline boiling products), 4,052,479 to Chang et al (operating conditions selected to restrict feed conversion to 5–25%) and 4,238,631 to Daviduk et al (riser reactor and dense fluid catalyst bed). U.S. Pat. No. 4,035,430 to Dwyer et al describes arranging the catalyst in a series of beds of increasing size with interstage quenching with methanol, dimethyl ether and/or light hydrocarbons for controlling exothermic heat. A tubular reactor is disclosed in U.S. Pat. No. 4,058,576 to Chang et al as a means of removing exothermic heat during the catalytic conversion of a lower alcohol to olefins. A two-stage conversion is employed, with an alcohol dehydration catalyst utilized in the first stage and a ZSM-5 zeolite catalyst in the second stage, which is a tubular reactor. In one embodiment, the ZSM-5 catalyst is located in the tubes of the reactor, with a heat transfer medium passed through the shell side of the reactor. As the reaction mixture passes through the catalyst, the exothermic heat of reaction released within the tubes is transferred to the heat exchange medium. No details are provided on the configuration of the tubular reactor, insofar as it may influence the thermal stability of the desired reaction. There is also no recognition in prior art of the criticality of maintaining proper temperature within the reactor and controlling the flow rate of the reactants to maintain the degree of conversion at such a level as to maximize the yield of ethylene.

U.S. patent application Ser. No. 577,456, which is incorporated herein by reference, discloses a method of partial conversion of methanol to hydrocarbon products rich in ethylene and other light olefins by employing a tubular heat-exchanger type reactor. However, the tubular reactor described therein may not guarantee stable reactor operation at partial conversion if catalysts exhibiting pronounced autocatalysis are employed.

U.S. patent application Ser. No. 632,739 discloses a method for improving the exothermic conversion of methanol to light olefins in a multistage fixed bed adiabatic reactor system by cofeeding small quantities of light olefins to methanol.

A primary concern in the tubular reactor design is the controllability of the operation. It is thus an object of this invention to provide a process for converting lower aliphatic alcohols, their corresponding ethers or mixtures of said alcohols and ethers to an olefinic product comprising primarily ethylene in a thermally stable manner.

It is another object of the present invention to provide a tubular reactor for converting methanol, dimethyl ether (DME) or a mixture of methanol and DME to an olefinic product in a thermally stable manner.

These and additional objects will become apparent to those skilled in the art from the following description of the invention.

SUMMARY OF THE INVENTION

It has now been found that the conversion of lower aliphatic alcohol having from 1 to 3 carbon atoms, e.g., methanol, its corresponding ether, DME, or mixtures of said alcohol and said ether, alone or in admixture with water, to olefinic hydrocarbon products in the presence of a zeolite catalyst, is provided in a tubular reactor, with increased stability in the tubular reactor. The operating performance of a tubular reactor system designed for exothermic conversion of methanol and/or DME to a hydrocarbon olefinic product can be improved by cofeeding small quantities of light olefins with the methanol and/or DME feed. The cofeeding of light olefins to either the dehydration or tubular reactor in order to improve reactor stability is unlike the light gas recycle system used in the prior art discussed above, in which the primary object is merely to provide a heat sink to control adiabatic temperature rise. In such a system, any inert light gas recycle could be used. The amount of cofed olefins in the present invention, typically from about 0.5% by weight of feed, is several orders of magnitude lower than the light gas recycle used in the conversion of methanol-to-gasoline boiling range hydrocarbons. Generally the feed is first contacted with a dehydration catalyst at elevated temperatures in a first dehydration reaction zone to obtain a product comprising a mixture of water and at least one ether. The product from the first reaction zone is thereafter contacted with a crystalline silicate zeolite in a second reaction zone at elevated temperatures and under exothermic reaction conditions to obtain the hydrocarbon products comprising olefins, the zeolite being a zeolite having a silica-to-alumina ratio of at least about 12, and a Constraint Index of about 1 to 12, and the second reaction zone comprising a tubular reactor wherein the crystalline silicate zeolite is confined within a plurality of adjacent elongated tubular reaction zones surrounded by a heat exchange fluid.

DETAILED DESCRIPTION OF THE INVENTION

Figure 1:
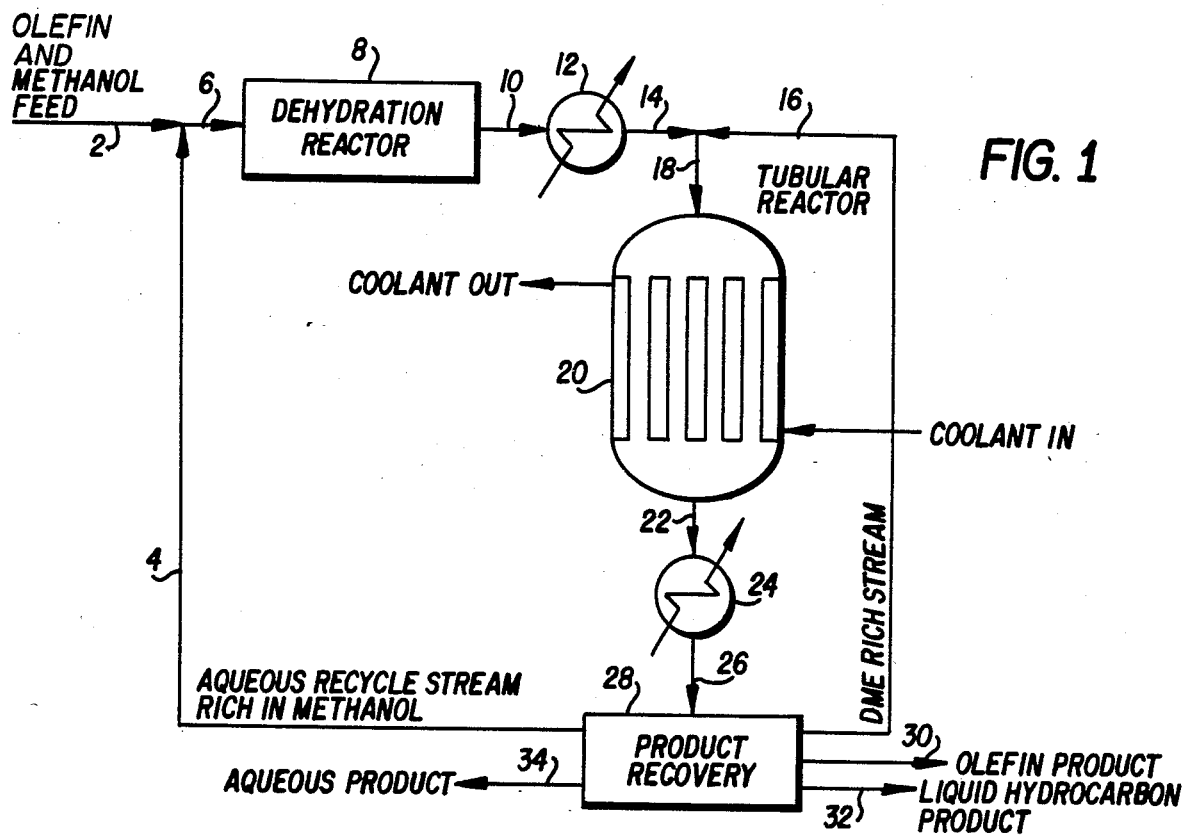

The feed used in the first stage of the process of the present invention comprises one or more lower aliphatic alcohols having 1 to 3 carbon atoms and/or corresponding ethers of such alcohols, providing that if alcohols other than methanol, or ethers other than dimethyl ether, are present in the feed, the feed comprises predominantly methanol alone or in admixture with dimethyl ether, or predominantly dimethyl ether. The term "predominantly", as used herein and in the appended claims, means that at least 15% by weight (wt %), preferably at least 70 wt %, and most preferably at least 80 wt %, of the total amount of oxygenates (alcohols and ethers) in the feed is comprised of methanol and/or dimethyl ether. It will be apparent to those skilled in the art that the feed may also contain water. Lower alcohols that may be used in the process of this invention include methanol, ethanol, propanol, and isopropanol. The feed may be comprised of a relatively pure single alcohol or mixtures of the alcohols. In general, any mixture comprising methanol, ethanol, propanol or isopropanol, and which is convertible with high exothermicity, is a suitable feed for the first reaction zone of the present invention. Conversions which produce more than about 100 BTU/lb of total hydrocarbon product, and preferably more than about 200 BTU/lb of total hydrocarbon product, at conversion temperature, are considered highly exothermic for the purposes of the present invention. In the preferred embodiment, the reactants comprise methanol or a mixture of methanol and dimethyl ether.

The composition of the hydrocarbon product obtained from the second stage of the reaction varies with catalyst type and process conditions. For ZSM-5 type catalysts, the ethylene yield (wt % of ethylene in the product based on the total amount of hydrocarbons in the product) is about 19 to about 35 wt %, preferably about 20 wt % to about 33 wt %, and most preferably about 22 wt % to about 32 wt %, propylene yield is about 6 to about 30 wt % and butenes yield is from about 4 to about 10 wt %. The yield of methane and ethane is low, typically less than 2 wt %. The balance of the hydrocarbon product is $C_3$ and $C_4$ paraffins and $C_5^+$ gasoline range hydrocarbons.

With an acidic zeolite of a relatively small particle size, such as erionite or ZSM-34 type catalysts, ethylene yield is about 30 to about 50 wt %, preferably about 35 wt % to about 50 wt %, and most preferably about 40 wt % to about 50 wt %, propylene yield is about 20 to about 35 wt %, and butenes yield is about 3 to about 5 wt %. The majority of the other hydrocarbon products is $C_1$-$C_4$ paraffins. The amount of $C_5^+$ hydrocarbons is typically less than 5 wt %.

The process of this invention is an improvement over the process disclosed and claimed in U.S. Pat. No. 4,058,576 to Chang et al and U.S. patent application Ser. No. 577,456, the entire contents of which are incorporated herein by reference.

In the preferred embodiment, the operation of the present invention comprises two sequential stages of catalytic contact, wherein both stages are heat generating operations. In the first stage, the catalytically exothermic heat generation is limited by restricting the conversion of methanol to approximately an equilibrium mixture, comprising dimethyl ether, methanol and water. The conversion product or first stage reaction effluent mixture, because of the catalytically generated exothermic heat, has a temperature of about 600° F. (315° C.) to about 750° F. (400° C.). The temperature of the first stage reaction effluent mixture is adjusted to a temperature within the range of about 520° F. (270° C.) to about 900° F. (480° C.), depending on the nature of the zeolite catalyst, by passing it through a suitable heat exchange means. A suitable heat exchange means is, for example, an indirect heat exchanger, wherein the heat exchange fluid is water or the methanol reactant passed to the first catalyst conversion stage.

In the first reaction zone, the feed is contacted with a dehydration catalyst to produce water and an equilibrium mixture of alcohol(s) and their corresponding ethers. The dehydration catalyst may be any catalyst which results in the intermolecular dehydration of the alcohol reactant to form an ether-rich product of higher carbon-to-oxygen ratio than the feed, such as a gamma alumina catalyst.

The dehydration reactions contemplated herein include those that form simple and mixed ethers, such as dimethyl ether or diethyl ether. These intermediates may be formed by the intermolecular dehydration of corresponding alcohol reactants, and such dehydration reactions are exothermic and generate heat. While the dehydration reaction itself is generally known with alumina compositions, such as gamma alumina, it is noted that other acidic catalysts known in the art, such as clays, silica-alumina and zeolites, are also effective dehydration catalysts.

Those skilled in the art will recognize that with methanol feed, no intramolecular dehydration is possible, and that therefore the dehydration reaction can only proceed exothermically to form, for example, dimethyl ether.

The second stage catalytic conversion operation of this invention is restricted to converting the first stage effluent mixture comprising alcohol, ether and water to an olefin-rich material. In the most preferred embodiment, wherein the feed in the first reaction zone is methanol, the first stage effluent mixture comprises methanol, dimethyl ether and water. The operation of the second reaction zone is highly exothermic and occurs rapidly in the presence of selected crystalline zeolites, and particularly a catalyst comprising either a ZSM-5 type crystalline zeolite or a small pore crystalline zeolite.

In general, the ZSM-5 type zeolite catalysts used in accordance with this invention are crystalline zeolites having a silica/alumina ratio of at least about 12 and a Constraint Index (CI) between about 1 and about 12. These zeolites and their use as conversion catalysts for lower aliphatic alcohols are described in U.S. Pat. Nos. 3,894,106; 4,025,571; 4,058,576; and 4,148,835. The entire contents of these patents are incorporated herein by reference.

The preferred class of zeolites described above are ZSM-5 type zeolites, as exemplified by ZSM-5, ZSM-11, ZSM-12, ZSM-22, ZSM-23, ZSM-35 and ZSM-38, with ZSM-5 being particularly preferred.

ZSM-5 is more particularly described in U.S. Pat. No. 3,702,886, the entire contents of which is incorporated herein by reference.

ZSM-11 is more particularly described in U.S. Pat. No. 3,709,979, the entire contents of which is incorporated herein by reference.

ZSM-12 is more particularly described in U.S. Pat. No. 3,832,449, the entire contents of which is incorporated herein by reference.

ZSM-22 is more particularly described in U.S. patent application Ser. No. 577,456, the entire contents of which have already been incorporated herein by reference.

ZSM-23 is more particularly described in U.S. Pat. No. 4,076,842, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

Particularly preferred catalysts within the above descriptions are ZSM-5 type zeolite catalysts made with large crystal ZSM-5, i.e., a crystal size of at least 1 micron, as described in U.S. Pat. Nos. 4,025,571 and 4,148,835, the entire contents of which are incorporated herein by reference. Another class of particularly preferred catalysts is ZSM-5 type catalysts which contain additional ingredients to improve ethylene selectively, such as amorphous silica interdispersed within the interior of the zeolite crystalline structure. Catalysts of this latter type are disclosed in U.S. Pat. Nos. 4,060,568 and 4,100,219, the entire contents of which are incorporated herein by reference.

In addition to the ZSM-5 zeolites, other zeolites, known in the art as small pore crystalline aluminosilicate zeolites, may be employed in accordance with the present invention. These small pore zeolites may be either naturally occurring or synthetic and include, by way of example, erionite, chabazite, Zeolite T, Zeolite ZK-5 and ZSM-34. Zeolite T is described in U.S. Pat. No. 2,950,952, Zeolite ZK-5 in U.S. Pat. No. 3,427,195, and ZSM-34 in U.S. Pat. Nos. 4,079,095 and 4,079,096, the entire contents of all patents are incorporated herein by reference. The crystal structure of this class of zeolites suitable for use as catalysts in the process of this invention is such as to provide access to and egress from the intracrystalline free space of the zeolites by virtue of having pores, the major dimension of which is greater than 3 but less than 6 angstrom units. These zeolites utilized herein are further characterized by pore windows of about a size such as would be provided by 8-membered rings of oxygen atoms. It will be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. The pores characterizing these zeolites useful in the present process may be substantially circular, such as in Zeolite ZK-5, having uniform pores of about 3.9 angstroms or somewhat elliptical, such as in erionite, having pores of approximately 3.6 by 5.2 angstroms. It will be understood that, in any case, the small pore zeolites used as catalysts in the process of this invention have a major pore dimension of less than 6 angstroms. The pore size dimensions of the above zeolites, as well as other feasible zeolites, are those specified in "Zeolite Frameworks" by W. M. Meier and D. H. Olson, appearing in *Advances in Chemistry Series,* Vol. 101, pages 155-170 (1971), the contents of which is incorporated herein by reference.

A convenient measure of the extent to which a zeolite provides control molecules of varying sizes to its internal structure is the Constraint Index of the zeolite. Zeolites which provide a highly restricted access to and egress from its internal structure have a high value for the Constraint Index, and zeolites of this kind usually have pores of small size. On the other hand, zeolites which provide relatively free access to the internal zeolite structure have a low value for the Constraint Index. The method by which Constraint Index is determined is described fully in U.S. Pat. No. 4,016,218, to which reference is made for details of the method.

Constraint Index (CI) values for some typical materials are:

|  | CI |
|---|---|
| ZSM-4 | 0.5 |
| ZSM-5 | 6-8 |
| ZSM-11 | 6-8 |
| ZSM-12 | 2 |
| ZSM-20 | 0.5 |
| ZSM-23 | 9.1 |
| ZSM-34 | 30-50 |
| ZSM-35 | 4.5 |
| ZSM-38 | 2 |
| ZSM-48 | 3.5 |
| TMA Offretite | 3.7 |
| TEA Mordenite | 0.4 |
| Clinoptilolite | 3.4 |
| Beta | 0.6-1.2 |
| Mordenite | 0.5 |
| REY | 0.4 |
| Amorphous Silica-Alumina | 0.6 |
| Dealiminized Y (Deal Y) | 0.5 |
| Chlorinated Alumina | *1 |
| Erionite | 38 |

*Less Than

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables, such as crystal size of the zeolite, the presence of occluded contaminants, etc., may effect the Constraint Index. Therefore, it will be appreciated that it may be possible to so select test conditions as to establish more than one value for the Constraint Index of a particular zeolite. This explains the range of Constraint Index for zeolites, such as ZSM-5, ZSM-12, ZSM-34 and Zeolite Beta.

In accordance with this invention, the conversion of olefinic hydrocarbons is accomplished, in the second reactor zone, in catalyst-containing reaction tubes of desired length and diameter to provide a sufficient contact time with the catalyst to accomplish the reaction desired. The second reaction zone comprises a plurality of adjacent catalyst-containing tubes of restricted cross-section to provide a desired heat transfer relationship between catalyst particles in the reaction tubes and a temperature controlling liquid medium circulated externally to the reaction tubes. Thus, the catalytic conversion operation in the second reaction zone producing olefins is performed in a plurality of adjacent reaction tubes parallel to each other, of restricted length and cross-section, each of which is in indirect heat exchange with a heat exchange fluid and sized to provide the reactant contact time and temperature restrictions as herein provided. Tubular reactors useful for the purposes of this invention are described in U.S. Pat. No. 4,058,576 and U.S. patent application Ser. No. 577,456, which have already been incorporated herein by reference.

The design of the tubular reactor is such that it assures that the conversion of feed in the tubular reactor is maintained at about 30% to 90% of oxygenates by weight. Maintaining the conversion level within those limits is critical for obtaining the desired relatively high ethylene contact in the product stream.

The reactor tube design selected must be satisfactory for accomplishing the exothermic heat transfer requirements expected under the reaction conversion conditions desired and occurring at reactant space velocities in the range of about 0.5 to 3.0 WHSV. During traverse of the reaction tubes, the first stage effluent mixture is converted with a selectivity and activity modified crystalline zeolite to produce an olefin rich product identified above. The olefin rich product formed in the second process stage is maintained at a temperature in the range of about 520° F. (270° C.) to about 700° F. (370° C.) during its passage through the second stage tubular reactor. Any suitable heat exchange fluid material may be used in indirect heat exchange relationship with the catalyst and reactants in the reaction tubes to remove the generated heat. Suitable heat exchanger materials are high-boiling organic (aromatic) liquids, molten salt and water. The product composition of the process of converting alcohols to olefins is extremely sensitive to even relatively small changes of the operating parameters, such as small temperature and space velocity deviations from the steady state conditions. Further, at higher temperatures of the reaction bed, conversion of the reaction increases rapidly, which, in turn, causes unexpectedly rapid decrease in the selectivity of the reaction to the ethylene product. This rapid decrease in ethylene selectivity is, unexpectedly, completely out of proportion to the relatively minor perturbations of steady state process conditions.

FIG. 1 is a schematic flow chart showing an example of a tubular reactor system as disclosed in U.S. patent application Ser. No. 577,456. With reference to FIG. 1, the methanol feed enters through line 2, where it is mixed with an aqueous product recycle stream rich in unreacted methanol from line 4 and passed into dehydration reactor 8, where the mixture is converted to an essentially equilibrium mixture of methanol, dimethylether (DME) and water by contacting it with a suitable catalyst, such as gamma alumina catalyst. This mixture exits the dehydration reactor through line 10 and may undergo either heating or cooling in heat exchanger 12, such that when it flows through line 14 and is combined with unreacted DME from line 16, the resulting mixture passing through line 18 is at the desired temperature for conversion. The combined stream flows through line 18 to a tubular reactor 20, which contains a series of tubes packed with ZSM-5 zeolite catalyst. The size of the tube is, for example, 2 inch diameter and 15 foot length. As the mixture passes through the reactor tubes, it is converted to an ethylene-rich hydrocarbon stream comprising about 19 wt % to about 35 wt % of ethylene, about 6 wt % to about 30 wt % of propylene and about 4 wt % to about 10 wt % of butylenes. The reaction is highly exothermic. The exothermic heat released in the tubular reactor is removed by means of a suitable coolant (e.g., molten salt, organic liquid or water) passing through the shell side of the reactor. The reactor effluent leaves the reactor through line 22, is cooled in heat exchanger 24, and enters a product recovery facility similar to that employed in conventional olefin plants. Alternatively, the gaseous hydrocarbon product containing DME may be processed by distillation to obtain the desired ethylene product and unreacted DME for recycle to the reactor. The ethylene containing product is recovered through line 30, while the DME is recycled through line 16.

The liquid hydrocarbon phase recovered through line 32 may be stabilized to recover light olefin products. The stabilized liquid hydrocarbon phase may be blended with gasoline-range components recovered from the olefins recovery facility to make either gasoline or a gasoline blending stock.

The aqueous liquid phase may be subjected to steam stripping, evaporation, and distillation to recover unreacted methanol and some water for recycle to the dehydration reactor through line 4. Surplus water is removed through line 34. It is not necessary to employ all three separation methods to obtain the desired recycle stream. Any unreacted DME present initially in the aqueous liquid phase will be recovered in the aqueous recycle stream (stream 4). Most of the water product produced by the conversion process in addition to non-chemically bound water present in the methanol feed is removed in stream 34.

The water content of the fresh methanol feed, i.e., without recycle, to this process can vary between a nominal zero up to about 70 wt %, preferably about 0 to 50 wt %. Any "equivalent" methanol-water feed may also be employed. A methanol-water feed is said to be "equivalent" to a given methanol-water feed when the methanol-water feed in question, plus any appropriate recycle streams recovered from the product of the subject conversion, produces a feed to the zeolite catalyst reactor which has substantially the same composition as the equilibrium mixture obtained when the given methanol-water feed is contacted with a dehydration catalyst.

In FIG. 1, the unreacted DME is recycled to the tubular reactor, rather than to the dehydration reactor. The former has an advantage over the latter, in that it allows a higher degree of conversion to be achieved in the dehydration reactor, thus reducing the heat load in the tubular reactor. In addition, since the reaction heat for converting DME to an olefinic hydrocarbon product is less than that for methanol, feeding unconverted DME directly to the tubular reactor also reduces the heat load on it. Because stable operation of the tubular reactor requires that the rate of heat removal with respect to temperature changes must be equal to or somewhat greater than the rate of heat generation with respect to temperature changes, the above scheme allows a tubular reactor to be operated in a stable manner over a wider range of conditions than otherwise possible. Of course, by being more restrictive on the tubular reactor operating conditions, it is possible to operate the dehydration reactor with feed streams 2, 4 and 16.

The following operating conditions may be usefully employed for a tubular reactor, which is preceded by a dehydration reactor processing recycle streams in addition to methanol feed. High operating pressures result in reduced yields of light olefins. Therefore, the inlet pressure to the tubular reactor should be less than about 40 psig. To provide sufficient heat transfer area with reasonable diameter tubes, the tube length should be 10–20 feed. Pressure drop and economic considerations indicate that the space velocity (expressed as weight hourly space velocity or WHSV) to the tubular reactor should be in the range of 0.5–3.0 $Hr^{-1}$. The operating temperature range for the tubular reactor is about 520° F. (270° C.) to about 700° F. (370° C.) for a ZSM-5 type zeolite and about 600° F. (315° C.) to about 900° F. (480° C.) for a small pore zeolite catalyst. Catalyst aging may be compensated for by raising the reactor temperature. It is preferred to use a catalyst made with a larger crystal ZSM-5 zeolite (at least about 1 micron) in the tubular reactor, such as that disclosed in U.S. Pat. Nos. 4,025,571 and 4,148,835. The ZSM-5 catalyst may be unsteamed or presteamed to reduce its hexane cracking activity (alpha value). Under the operating conditions described herein, the alpha value should exceed 20. The catalyst may also contain additional ingredients which improve ethylene selectivity, such as, e.g., intracrystalline silica, as described in U.S. Pat. Nos. 4,060,568 and 4,100,219. Of course, other suitable catalysts may also be employed.

It is preferred to limit the overall conversion level to hydrocarbons of methanol and DME to between about 10 and 90%. At higher conversion levels, significant quantities of the methanol will be converted to aromatic compounds, even at temperatures within the preferred range. To ensure partial conversion, it is essential that the reactor configuration and operating conditions do not result in an unstable or sensitive reactor operation (i.e., small perturbations in the operating conditions lead to excessive temperature rise and hence excessive conversion of desirable light olefins to gasoline boiling-range components). Thus, although the methanol conversion reaction at partial conversion can be advantageously carried out in a tubular reactor, it is critical to restrict the amount of heat generated in an individual reaction zone to prevent excessive conversion of desired light olefin products.

In accordance with the present invention, the stability of a tubular reactor is achieved by cofeeding small amounts of light olefins, with the methanol feed entering the reactor either at lines 2 or 18 in FIG. 1.

The conversion of methanol to olefinic and gasoline boiling hydrocarbons can be represented by a non-linear autocatalytic kinetic model, which can be described as follows:

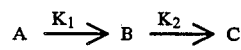

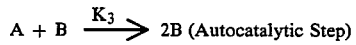

where,
A represents the $CH_2$ in oxygenates (Methanol/DME);

B represents light olefins ($C_2$, $C_3$, $C_4$); and

C represents other hydrocarbons (paraffins, aromatics, naphthenes and heavy olefins).

The degree of autocatalysis in the above model is dependent upon the relative magnitude of $K_1$ and $K_3$. When there are no light olefins (B) in the feed and $K_1$ is small compared to $K_3$, there is an occurrence of strong autocatalysis. However, if $K_1$ is sufficiently large compared to $K_3$, reaction can be approximated by pseudo-first order kinetics, as illustrated in Example 1 below.

Using the above kinetic model, the behavior of a tubular reactor system for various values of kinetic parameters and feed conditions has been simulated.

The following examples best illustrate the present invention.

EXAMPLE 1

The example illustrates the methanol conversion reaction to light olefin products on different HZSM-5C catalysts in an isothermal laboratory reactor. The data, illustrated in FIG. 2, suggests a change in the nature of methanol conversion reactions as the catalyst is deactivated by presteaming. Three catalysts were examined under the conditions listed below:

Catalyst 1 - fresh, unsteamed HZSM-5C (alpha = 180)
  Pressure, psig = 5
  Temperature, °F. (°C.) = 600 (315)
Catalyst 2 - deactivated, presteamed HZSM-5C (alpha = 24)
  Pressure, psig = 25
  Temperature, °F. (°C.) = 600 (315)
Catalyst 3 - presteamed HZSM-5C (alpha = 70)
  Pressure, psig = 5
  Temperature, °F. (°C.) = 650 (340)

Figure 2:
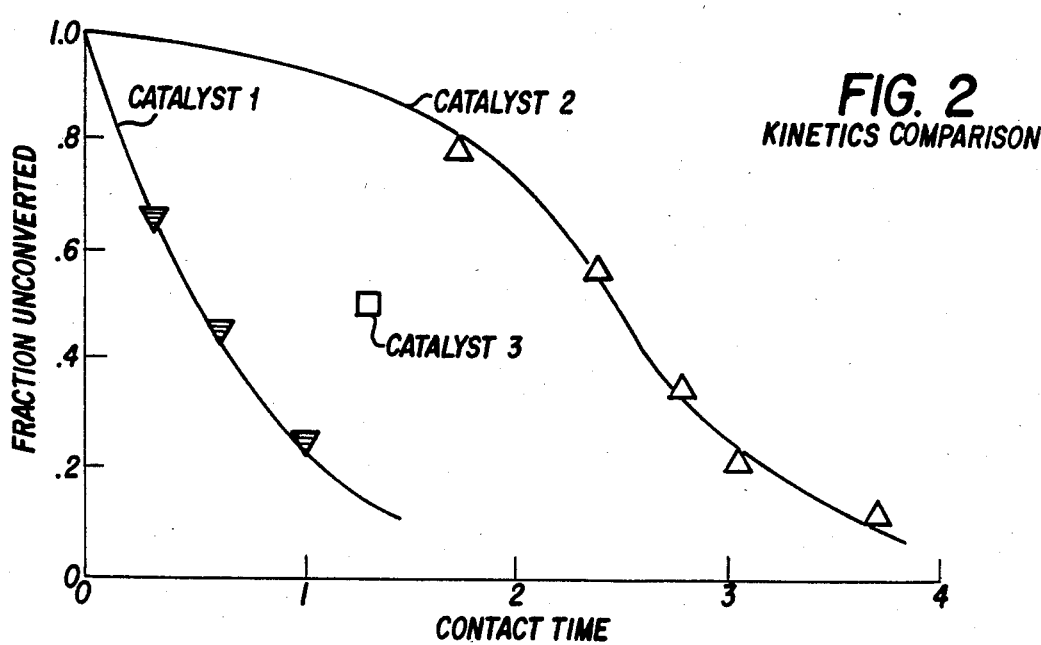

As can be seen in FIG. 2, there is a marked difference in the kinetics behavior between Catalyst 1 and Catalyst 2. The kinetic behavior of Catalyst 1 is approximated by a pseudo-first order reaction, i.e., the reaction rates (slopes of the tangents to the solid line in FIG. 2) decrease continuously with increased contact times. For Catalyst 2, there is shown a prolonged induction period of low reaction rates, followed by an acceleration period in the reaction rates. At the point of high conversion or when the feed has been in contact with the catalyst for an extended time, the reaction rate decreases. This behavior is typical for a catalyst exhibiting pronounced autocatalysis. FIG. 2 also illustrates experimental observation Catalyst 3. Prior studies with this catalyst in a multistage adiabatic reactor (U.S. patent application Ser. No. 632,739) suggest some degree of autocatalysis. Thus, the degree of autocatalysis appears to be a function of the extent of catalyst deactivation.

EXAMPLE 2

This example illustrates the simulation of a tubular reactor employing Catalyst 2 from Example 1. It has previously been found that for fresh HZSM-5C, Catalyst 1, wherein $K_3$ is essentially zero, a stable controllable tubular reactor can be operated under the following conditions:

Tube Diameter, in = 1.5
Tube Length, ft = 12
WHSV, $Hr^{-1}$ = 0.5-3
Feed = 50/50 (Methanol/Water)
Conversion, % = 50

Figure 3:
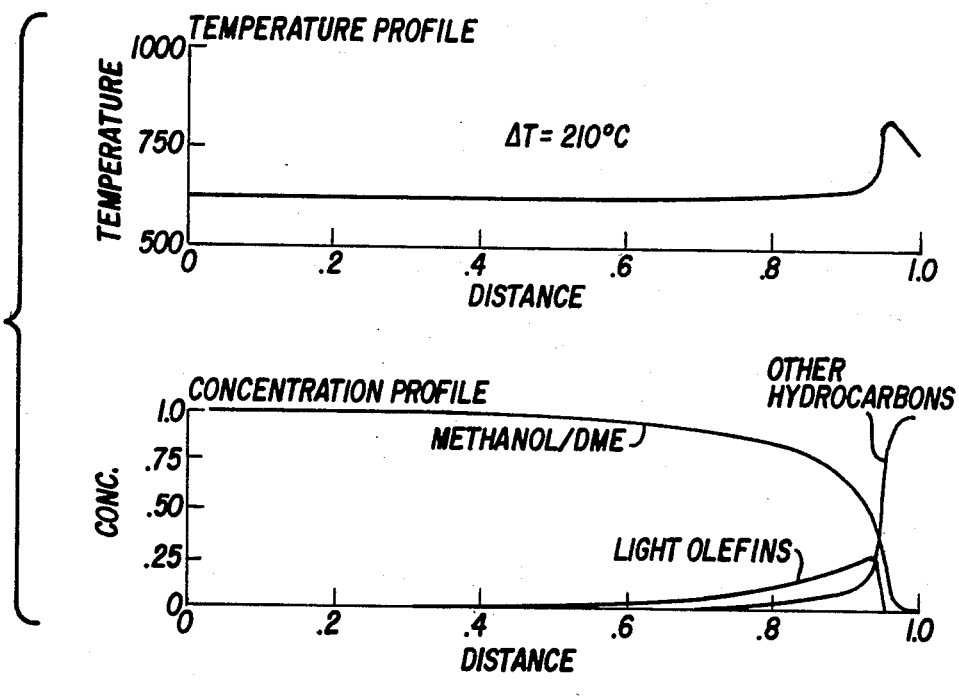

Referring now to FIG. 3, it can be seen that if Catalyst 2 is substituted for Catalyst 1, the tubular reactor cannot be operated stably at partial conversion. From the concentration profiles of FIG. 3, it can be seen that the conversion reaction has a prolonged induction period and, once the reaction accelerates, it reaches 100% conversion. From the temperature profile in FIG. 3, it can be seen that most of the heat is generated in a narrow section of the bed, resulting in a severe hot spot. This type of operation is undesirable for the MTC process.

EXAMPLE 3

Figure 4:
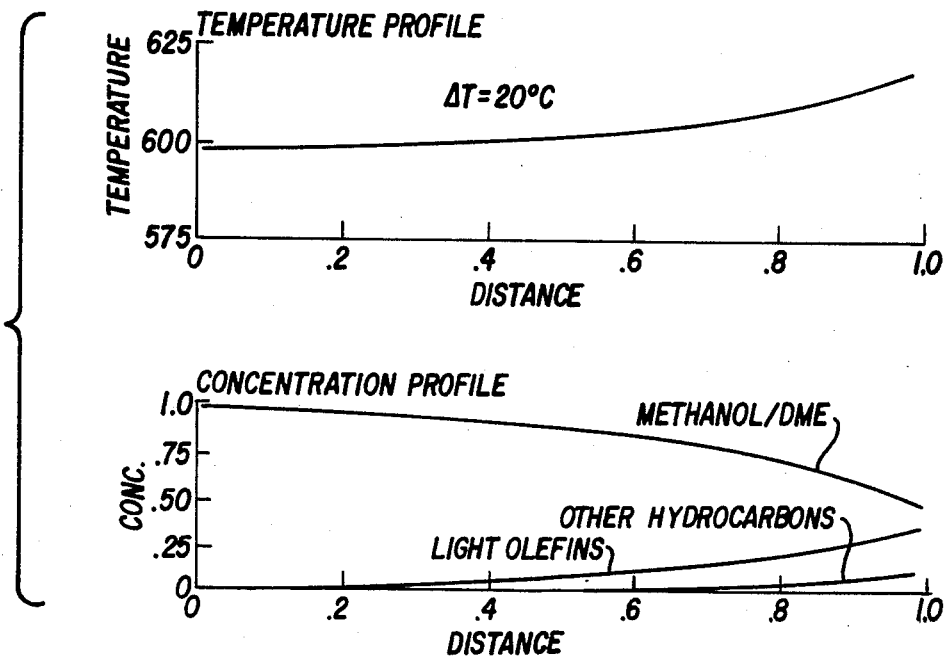

This example illustrates the simulation of a tubular reactor when small amounts of light olefins are cofed with the feed. Referring now to FIG. 4, in which 1.5 wt % light olefin is used, it can be seen that the temperature rise is much more gradual than that shown in Example 2, and the changes in the rates of reactions are not significantly large. The, light olefin cofeeding will necessitate lowering the inlet temperature somewhat due to increased overall rates of methanol-DME conversion reactions. This example illustrates that olefin cofeeding will allow a tubular reactor system to operate stably at partial conversion (10–90%).

In a commercial operation, it is conceivable to utilize ethylene, propylene or butene, which would act as the autocatalytic agent to initiate the methanol conversion reaction. A small portion of the product stream containing light olefins could also be recycled. For stable tubular reactor operations at partial conversion, it is preferable to recycle less than 3 wt % light olefins, depending upon the operating conditions.

Thus, light olefin cofeeding in a tubular reactor system is necessary for catalysts exhibiting pronounced autocatalysis. Even though it has been shown that fresh HZSM-5C does not exhibit complications in tubular reactor stability due to autocatalysis, the use of an olefin cofeed is suggested in order to overcome anticipated problems in a commercial reactor after prolonged use of the catalyst, which may undergo several cycles of operation and regeneration.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. In the process of converting a feed comprising at least one lower aliphatic alcohol having from 1 to 3 carbon atoms and/or corresponding ethers of such alcohols, alone or in admixture with water, into a predominantly olefinic hydrocarbon product comprising at least 50 wt. % olefins, wherein said feed is contacted with a dehydration catalyst at elevated temperatures in a first reaction zone comprising a dehydration reactor to obtain a product comprising a mixture of water and at least one ether, and said product from said first reaction zone is thereafter contacted with a crystalline silicate zeolite in a second reaction zone at elevated temperatures and under exothermic reaction conditions to obtain said hydrocarbon products comprising olefins, said zeolite being a zeolite having a silica-to-alumina ratio of at least about 12, and a Constraint Index of about 1 to 12, and said second reaction zone comprising a tubular reactor wherein said crystalline silicate zeolite is confined within a plurality of adjacent elongated tubular reaction zones, the improvement comprising cofeeding with said feed about 0.5–3% by weight of said feed a light olefin to said dehydration reactor to stabilize the conversion operation.

2. The process of claim 1, wherein said aliphatic alcohol is methanol and said ether is dimethyl ether.

3. The improvement of claim 1, wherein said cofed light olefin comprises $C_2$–$C_4$ olefins.

4. The improvement of claim 1, wherein said cofed olefin is propylene.

5. The improvement of claim 1, wherein the amount of cofed olefin is no greater than 1.5% by weight of said ether-rich product.

6. The improvement of claim 1, wherein the amount of cofed light olefin is about 0.7% by weight.

7. The improvement of claim 1, wherein said cofed light olefin is formed by cofeeding the corresponding alcohol of said light olefin with said aliphatic alcohol feed for contact over said dehydration catalyst.

8. The improvement of claim 7, wherein said cofed olefin is propylene, said propylene being produced by cofeeding isopropanol for contact with said dehydration catalyst.

9. The improvement of claim 1, wherein said crystalline aluminosilicate zeolite present in said fixed beds is ZSM-5 zeolite.

10. The improvement of claim 9, wherein the ZSM-5 zeolite has a crystal size of at least about 1 micron.

11. The improvement of claim 9, wherein amorphous silica is interdisposed within the interior of said crystalline structure of said zeolite.

12. The improvement of claim 1, wherein said crystalline aluminosilicate zeolite present in said fixed beds is erionite or ZSM-34.

13. The improvement of claim 1, wherein the dehydration catalyst is gamma alumina.

14. The improvement of claim 1, wherein the feed contacted in the first reaction zone is a methanol-water mixture containing about 0 to 70% by weight water or an equivalent methanol-water mixture.

15. The improvement of claim 14, wherein the exothermic reaction conditions in the second reaction zone include a pressure of less than 50 psig and a space velocity of 0.5–3.0 WHSV.

16. The improvement of claim 9, wherein the elevated temperature in the second reaction zone are in the range of about 520° F. (270° C.) to about 700° F. (370° C.).

17. The improvement of claim 12, wherein the elevated temperatures in the second reaction zone are in the range of about 600° F. (315° C.) to about 900° F. (480° C.).

18. The improvement of claim 1, wherein the temperature in both reaction zones is increased to compensate for catalyst aging.

19. The improvement of claim 9, wherein the ZSM-5 zeolite is presteamed.

20. The improvement of claim 19, wherein the diameter of said elongated tubes is less than 2 inches.

21. The improvement of claim 9, wherein said hydrocarbon products comprise about 19 to 35% by weight of ethylene, about 6 to 30% by weight of propylene and about 4 to 10% by weight of butenes.

22. The improvement of claim 12, wherein said hydrocarbon products comprise about 30 to 50% by weight of ethylene, about 20 to 35% by weight of propylene and about 3 to 5% by weight of butenes.

23. The improvement of claim 1, wherein the predetermined conversion of said feed to said hydrocarbon products is between about 10 and about 90%.

24. In the process of converting a feed comprising methanol and/or dimethyl ether, alone or in admixture with water, into a predominantly olefinic hydrocarbon product comprising at least 50 wt. % olefins, wherein said feed is contacted with a dehydration catalyst in a dehydration reactor at elevated temperatures in a first reaction zone to obtain a product comprising a mixture of water and at least one ether, and said product from said first reaction zone is thereafter contacted with a crystalline silicate zeolite in a second reaction zone at elevated temperatures and under exothermic reaction conditions to obtain said predominantly olefinic hydrocarbon product, said zeolite being a zeolite having a silica-to-alumina ratio of at least about 12, and a Constraint Index of about 1 to 12, and said second reaction zone comprising a tubular reactor wherein said crystalline silicate zeolite is confined within a plurality of adjacent elongated tubular reaction zones, the improvement comprising cofeeding with said feed about 0.7% by weight of said feed $C_2$–$C_4$ olefins to said dehydration reactor to stabilize the conversion operation.

25. The improvement of claim 24, wherein said crystalline silicate zeolite is presteamed ZSM-5 having a crystal size of at least about 1 micron.

* * * * *